United States Patent
Baker et al.

(10) Patent No.: US 9,476,061 B2
(45) Date of Patent: Oct. 25, 2016

(54) ADENOVIRAL VECTORS FOR TRANSDUCTION OF VASCULAR TISSUE

(71) Applicant: Crucell Holland B.V., Leiden (NL)

(72) Inventors: Andrew Baker, Glasgow (GB); Stuart Nicklin, Glasgow (GB); Alan Parker, Glasgow (GB)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 0 days.

(21) Appl. No.: 14/402,791

(22) PCT Filed: May 23, 2013

(86) PCT No.: PCT/EP2013/060589
§ 371 (c)(1),
(2) Date: Nov. 21, 2014

(87) PCT Pub. No.: WO2013/174910
PCT Pub. Date: Nov. 28, 2013

(65) Prior Publication Data
US 2015/0203869 A1  Jul. 23, 2015

Related U.S. Application Data

(60) Provisional application No. 61/651,400, filed on May 24, 2012.

(30) Foreign Application Priority Data

May 24, 2012 (EP) .................... 12169347

(51) Int. Cl.
| | | |
|---|---|---|
| A61K 48/00 | (2006.01) |
| C12N 15/86 | (2006.01) |
| C12N 15/63 | (2006.01) |
| C12N 5/10 | (2006.01) |
| C12N 15/85 | (2006.01) |
| C12N 15/861 | (2006.01) |
| A61K 35/44 | (2015.01) |
| C12N 7/00 | (2006.01) |

(52) U.S. Cl.
CPC .............. *C12N 15/85* (2013.01); *A61K 35/44* (2013.01); *C12N 7/00* (2013.01); *C12N 15/861* (2013.01); *A61K 48/00* (2013.01); *C12N 2710/10042* (2013.01); *C12N 2710/10043* (2013.01)

(58) Field of Classification Search
CPC ...... A61K 48/00; C12N 15/63; C12N 15/86; C12N 15/861; C12N 5/0602; C12N 5/069; C12N 5/0691; C12N 5/10
USPC .............. 514/44 R; 424/93.21, 199.1, 233.1; 435/325, 456, 320.1
See application file for complete search history.

(56) References Cited

U.S. PATENT DOCUMENTS

2005/0084480 A1  4/2005  Bout et al.

FOREIGN PATENT DOCUMENTS

| WO | 99/55132 A2 | 11/1999 |
| WO | 00/70071 A1 | 11/2000 |
| WO | 02/40665 A2 | 5/2002 |
| WO | 03/104467 A1 | 12/2003 |

OTHER PUBLICATIONS

Wolff et al. (2006) J. Vasc. Surg., vol. 43, 1028-1036.*
Lemckert et al. (2006) J. Gen. Virol., vol. 87, 2891-2899.*
George et al. (2000) Circulation, vol. 101, 296-304.*
Moutabarrik et al. (1993) Lymphokine Cytokine Research, vol. 12(3), 167-172.*
Alba et al. (2005) Gene Therapy, vol. 12, S18-S27.*
Abbink, P. et al., Comparative seroprevalence and immunogenicity of six rare serotype recombinant adenovirus vaccine vectors from subgroups B and D. Journal of virology 81, 4654 (2007).
Abrahamsen et al., J. Virol 71: 8946-51 (1997).
Akowuah, E.F. et al., Preventing saphenous vein graft failure: Does gene thereapy have a role? Annals of Thoracic Surgery 76, 959 (2003).
Alba et al. Gene Ther. 8, 1347-1353 (2005).
Arnberg, N. Adenovirus receptors: implications for tropism, treatment and targeting. Reviews in Medical Virology 19, 165 (2009).
Brough, et al., J. virol 70: 6497-501 (1996).
Carlino, M. et al. Prevention of distal embolization during saphenous vein graft lesion angioplasty—Experience with a new temporary occlusion and aspiration system. Circulation 99, 3221 (1999).
Cheng, Y.H. et al., MicroRNA-145, a Novel Smooth Muscle Cell Phenotypic Marker and Modulator, Controls Vascular Neointimal Lesion Formation. Circulation Research 105, 158 (2009).
Danthinne, X. et al. Production of first generation adenovirus vectors: a review. Gene Therapy 7, 1707 (2000).
Davies, M.J. Pathophysiology of acute coronary syndromes, Indian Heart J. 52, 473 (2000).
De Jong et al. Lancet 1 (8337): 1293-1296 (1998).
Edgar, Nucleic Acids Res. 32(5); 1792-1797 (2004).
Francki et al. Arch. Virol. Suppl. 2: 140-144 (1991).
Fuster, J.J. et al. Control of cell proliferation in atherosclerosis: insights from animal models and human studies. Cardiovascular Research 86, 254 (2010).
Gaffney, M.M. et al. Cardiovascular gene therapy: current status and therapeutic potential. British Journal of Pharmacology 152, 175 (2007).
George, S.J. et al. Inhibition of late vein graft neointima formation in human and porcine models by adenovirus-mediated overexpression of tissue iinhibitor of metalloproteinase-3, Circulation, 101(3), 296-304 (2000).

(Continued)

*Primary Examiner* — Anne Marie S Wehbe
(74) *Attorney, Agent, or Firm* — Panitch Schwarze Belisario & Nadel LLP

(57) ABSTRACT

The invention relates to the field of gene transfer, and in particular to the use of adenoviral vectors of serotype Ad49 for gene delivery to vascular tissue.

15 Claims, 5 Drawing Sheets

(56) References Cited

OTHER PUBLICATIONS

George, S.J. et al. Wild-type p53 gene transfer inhibits neointima formation in human saphenous vein by modulation of smooth muscle cell migration and induction of apoptosis, Gene Therapy, 8(9) 668-76 (2001).
Grabow, N. et al. Absorbable polymer stent technologies for vascular regeneration. Journal of chemical Technology and Biotechnology 85, 744 (2010).
Hierholzer et al., J. Infect. Dis. 158, 804-813 (1988).
Howitt, J. et al., Structural basis for variation in adenovirus affinity for the cellular coxsackievirus and adenovirus receptor. Journal of Biological Chemistry 278, 26208 (2003).
Kitamura, S. et al., Excellent Patency and growth-potential of internal mammary artery grafts in pediatric coronary-artery bypass surger—new evidence for a live conduit. Circulation 78, 129 (1988).
Kritz, A.B. et al. In vivo modulation of Nogo-B Attenuates Neointima formation, Molecular Therapy 16 (11) 1798-804 (2008).
Libby, P. et al., pathophysiology of coronary artery disease. Circulation 111, 3481 (2005).
Nan et al. Gene Therapy 10: 326-36 (2003).
Nettlebeck, D.M. et al. Molecular Therapy, Academic Press, San Diego, CA vol. 3, No. 6, Jun. 1, 2001.
Newby, A.C. et al. Molecular mechanisms in intimal hyperplasia. Journal of Pathology 190, 300 (2000).
Nicklin, S.A. et al. The influence of adenovirus fiber structure and function on vector development for gene therapy. Molecular Therapy 12, 384 (2005).
Owens, G.K. et al. Molecular regulation of vascular smooth muscle cell differentation in development and disease. Physiological Reviews 84, 767 (2004).
Preuss, M.A. et al. Enhanced gene delivery to human primary endothelial cells using tropism-modified adenovirus vectors. The Open Gene Therapy Journal, vol. 1, No. 1, Jan. 1, 2008.
Purcell, C. et al. Neo-intimal hyperplasia in vascular grafts and its implications for autologous arterial grafting. Annals of the Royal College of Surgeons of England 79, 164 (1997).
Raper, S.E. et al. Fatal systemic inflammatory response syndrome in a ornithine transcarbamylase deficient pateitn following adenoviral gene transfer. Molecular Genetics and Metabolsm 80, 148 (2003).
Rux, J.J. et al. Adenovirus structure. Human Gene Therapy 15, 1167 (2004).
Schnurr, D. et al. Adenovirus mixture isolated from the brain of an aids patient with encephalitis. Journal of Medical virology 47, 168 (1995).
Schnurr, D. et al. 2 New Candidate adenovirus serotypes, Intervirology 36, 79-83 (1993).
Thorner, A.R. et al. Age dependence of adenovirus-specific neutralizing antibody titers in individuals from sub-Saharan Africa. Journal of clinical Microbiology 44, 3781 (2006).
Turunen, P. Extracellular superoxide dismutase with caccinia virus anti-inflammatory protein 35K or tissue inhibitor of metalloproteinase-1: Combination gene therapy in the treatment of vein graft stenosis in rabbits. Human Gene Therapy 17, 405 (2006).
Young, L.S. et al. Viral gene therapy strategies: from basic science to clinical application. Journal of Pathology 208, 299 (2006).
Lemckert, A.A.C. et al. Generation of a novel replication-incompetent adenoviral vector derived from human adenovirus type 49: manufacture on PER.C6 cells, tropism and immunogenicity. Journal of General Virology 87, 2891-2899 (2006).
Stone, D. et al, Journal of Endocrinology 164, 103-118 (2000).
International Search Report dated Jul. 26, 2013 in PCT/EP2013/060589.
International Preliminary Report on Patentability dated Aug. 20, 2014 in PCT/EP2013/060589.

\* cited by examiner

```
Hexon (protein id=ABD52395.1; GI:88810182)
MCLTARERAKMATPSMMPQWAYMHIAGQDASEYLSPGLVQFARA
TDTYFSLGNKFRNPTVAPTHDVTTDRSQRLTLRFVPVDREDTTYSYKARFTLAVGDNR
VLDMASTYFDIRGVLDRGPSFKPYSGTAYNSLAPKGAPNSSQWDAKENNGQGEAKTHT
YGVAAMGGYNITKDGLQIGIDENKEEDEEGREIFAVKSYQPEPQVGEENWQNTENFYG
GRALKKETKMKPCYGSFARPTNDKGGQAVFKTGENGKPTEELDIDLAFFDLRQNDTGG
NNNQPDMIMYAENVNLETPDTHVVYKPGTSDDSSEINLCQQSMPNRPNYIGFRDNFVG
LMYYNSTGNMGVLAGQASQLNAVVDLQDRNTELSYQLLLDSLGDRTRYFSMWNSAVDS
YDPDVRIIENHGVEDELPNYCFPLDGSGSSTAYQGVEPDTTVAGTNDKWKVNAKVAQH
NQIAKGNLFAMEINLQANLWKSFLYSNVALYLPDSYKYTPANVKLPTNTNTYDYMNGR
VVAPSLVDAYINIGARWSLDPMDNVNPFNHHRNAGLRYRSMLLGNGRYVPFHIQVPQK
FFAIKNLLLLPGSYTYEWNFRKDVNMILQSSLGNDLRVDGASVRFDSVNLYATFFPMA
HNTASTLEAMLRNDTNDQSFNDYLSAANMLYPIPAKATNVPISIPSRNWAAFRGWSFT
RLKTKETPSLGSGFDPYFVYSGSIPYLDGTFYLNHTFKKVSIMFDSSVSWPGNDRLLT
PNEFEIKRSVDGEGYNVAQCNMTKDWFLVQMLSHYNIGYQGFHVPEGYKDRMYSFFRN
FQPMSRQVVDEINYKDYKAVTLPFQHNNSGFTGYLAPTMRQGQPYPANFPYPLIGSTA
VPSVTQKKFLCDRVMWRIPFSSNFMSMGALTDLGQNMLYANSAHALDMTFEVDPMDEP
TLLYLLFEVFDVVRVHQPHRGVIEAVYLRTPFSAGNATT
```

FIG. 8

```
Fiber (protein id=ABD52400.1; GI:88810187)
MSKRLRVEDDFNPVYPYGYARNQNIPFLTPPFVSSDGFQNFPPG
VLSLKLADPIAITNGNVSLKVGGGLTVEQDSGNLKVNPKAPLQVATDNQLEISLADPF
EVKNKKLSLKVGHGLKVIDENISTLQGLLGNLVVLTGMGIGTEELKKDDKIVGSAVNV
RLGQDGGLTFDKKGDLVAWNKENDRRTLWTTPDPSPNCKVSEEKDSKLTLVLTKCGSQ
ILASVSLLVVKGKFANINNKTNPGEDYKKFSVKLLFDANGKLLTGSSLDGNYWNYKNK
DSVIGSPYENAVPFMPNSTAYPKIINNGTANPEDKKSAAKKTIVTNVYLGGDAAKPVA
TTISFNKETESNCVYSITFDFAWNKTYKNVPFDSSSLTFSYIAQDAEDKNE
```

FIG. 9

```
Penton (protein id=ABD52391.1; GI:88810178)
MRRAVVSSSPPPSYESVMAQATLEVPFVPPRYMAPTEGRNSIRY
SELAPQYDTTRVYLVDNKSADIASLNYQNDHSNFLTTVVQNNDFTPAEASTQTINFDE
RSRWGGDLKTILHTNMPNVNEYMFTSKFKARVMVSRKRPEGATDASQDILKYEWFEFT
LPEGNFSETMTIDLMNNAILENYLQVGRQNGVLESDIGVKFDSRNFRLGWDPETKLVM
PGVYTYEAFHPDVVLLPGCGVDFTESRLSNLLGIRKKQPFQEGFRIMYEDLEGGNIPA
LLDVEAYLKSKNDLEEATKNANRAAANGGGETRGDTFLTTEQLRAAGKELVIKPIKED
ASKRSYNVIGDTHDTLYRSWYLSYTYGDPEKGVQSWTLLTTPDVTCGAEQVYWSLPDL
MQDPVTFRSTQQVSNYPVVGAELMPFRAKSFYNDLAVYSQLIRSYTSLTHVFNRFPDN
QILCRPPAPTITTVSENVPALTDHGTLPLRSSIRGVQRVTVTDARRRTCPYVYKALGI
VAPRVLSSRTF
```

FIG. 10

ADENOVIRAL VECTORS FOR TRANSDUCTION OF VASCULAR TISSUE

CROSS-REFERENCE TO RELATED APPLICATIONS

This application is a Section 371 of International Application No. PCT/EP2013/060589, filed May 23, 2013, which was published in the English language on Nov. 28, 2013 under International Publication No. WO 2013/174910 A1, which claims the benefit under 35 U.S.C. §119(e) of U.S. Provisional Patent Application No. 61/651,400, filed May 24, 2012, and the disclosures of which are incorporated herein by reference.

REFERENCE TO SEQUENCE LISTING SUBMITTED ELECTRONICALLY

This application contains a sequence listing, which was submitted electronically via EFS-Web. The sequence listing submitted via EFS-Web is part of the specification and is herein incorporated by reference in its entirety.

FIELD OF THE INVENTION

The invention relates to the field of gene transfer, and in particular to the use of adenoviral vectors for gene delivery to vascular tissue.

BACKGROUND TO THE INVENTION

Adenoviruses (Ads) are the most widely used vectors in gene therapy. They have the advantages of having the ability to infect a wide range of dividing and non-dividing cells, of being easily produced to high titers, and of having well characterized strains used for construction of recombinant viruses (especially the ones being commonly used in gene therapy such as Ad2, Ad5). The first generation E1/E3 deleted vectors can accommodate ~8 kb of inserts whereas helper dependent Ads can accommodate up to 37 kb of foreign genetic material.[16]

Ads were first isolated and cultured in 1953 from adenoid cells and to date 55 human adenovirus serotypes have been identified and grouped in six species (A-F). Most of these serotypes cause mild infection of the upper respiratory tract, gastroenteritis or conjunctivitis. Moreover, wildtype (WT) adenovirus has been used as a vaccine for US military recruits and showed to cause very few side effects. This contributed to the idea that Ads are safe viruses to use for human gene therapy, although high doses of adenovirus may cause an overwhelming immune response.[17, 18, 19] However, local ex vivo gene transfer reduces these problems.

A significant limitation of using Ads as vectors clinically is the high rates of pre-existing neutralising antibodies in most humans leading to rapid neutralization upon administration in the circulation. Furthermore, upon administration into in the circulation the majority of virus particles are rapidly sequestered by the liver, thus failing to reach their target cells or tissues to a sufficient extent for their intended purpose. Moreover, increasing the vector dosage as an attempt to overcome these problems has proven to be inadequate and sometimes toxic, or even lethal.

Adenovirus serotype 5 (Ad5) is widely used for vascular gene transfer, where delivery of therapeutic transgenes to prevent excessive smooth muscle cell proliferation can prevent neointimal thickening and thus graft failure following coronary bypass procedures. However, uptake of adenovirus into the vessel wall and the resulting level of gene transfer mediated through Ad5 is relatively poor and necessitates high input titers of virus. Additionally, a significant proportion of patients present pre-existing neutralising antibodies against Ad5.

Collectively, these sub-optimal characteristics of Ad5 limit the progression and interpretation of vascular gene therapy in the clinical setting. Thus, identification and development of more efficient vectors is needed.

Some workers have moved towards vectors based on other virus types entirely. Those choosing to persist with adenoviruses have adopted strategies including use of chimeric human Ads (Ad pseudotypes), non-human Ads, or Ad vectors with low seroprevalence in order to avoid the immune response and detarget the vectors away from the liver and retarget them to cells and tissues of interest.

However, the human adenovirus family is extensive with many rare and understudied adenoviruses (currently 55 known serotypes). At present, little is known about their tropism or potential for use as novel vectors, seriously limiting their practical application.

SUMMARY OF THE INVENTION

The inventors have now discovered that adenovirus serotype 49 (Ad49), a rare species D adenovirus, has surprisingly high tropism and infectivity for vascular tissue, making it ideal for vascular gene delivery. Transduction is rapid, rendering ex vivo gene delivery feasible in the narrow window of opportunity provided during vascular surgery. In addition, the majority of the population has little or no pre-existing immunity to Ad49, making it suitable for gene delivery performed in vivo, as well as methods performed in vitro or ex vivo.

Accordingly, in a first aspect, the present invention provides a method of gene delivery to a vascular cell or tissue comprising contacting said vascular cell with an adenoviral gene delivery vehicle, wherein the adenoviral gene delivery vehicle comprises an Ad49 major capsid protein.

The method may be performed in vivo. In such an aspect, the invention provides a method of gene transfer to a subject in need thereof, comprising administering an adenoviral gene delivery vehicle to the subject, wherein the adenoviral gene delivery vehicle comprises an Ad49 major capsid protein.

The method may also be performed in vitro or ex vivo. For example, the method may be applied to a vascular cell or tissue intended for introduction to a subject, e.g. a vascular tissue graft.

Thus the invention provides a therapeutic or prophylactic method comprising the steps of providing a vascular cell or tissue, contacting the cell or tissue with an adenoviral gene delivery vehicle to provide genetically modified cell or tissue, and introducing the genetically modified cell or tissue to a subject, wherein the adenoviral gene delivery vehicle comprises an Ad49 major capsid protein.

The term "vascular" is used in this specification to refer to blood vessels, primarily veins and arteries, but encompassing other vessel types such as arterioles, venules and capillaries where the context permits.

The vascular cell or tissue to be transduced may comprise one or more vascular endothelial cells (ECs) and/or one or more vascular smooth muscle cells (SMCs). It may comprise a length of blood vessel, e.g. a length of vein or artery.

The cell or tissue may have been obtained directly from the subject (or, less frequently, from a third party donor) prior to being contacted with the adenoviral gene delivery vehicle, for example, as part of the same surgical procedure. Such methods are generally referred to as ex vivo gene delivery methods. In such cases the length of blood vessel is typically an explant, derived, for example, from saphenous vein, internal mammary artery (e.g. left internal mammary artery), gastroepiploic artery (e.g. right gastroepiploic artery), and inferior epigastric artery.

In such ex vivo methods, it is desirable that grafting of the vascular explant occurs as soon as possible after its extraction. In practice this allows a window of one hour or less, and often 30 minutes or less, for gene delivery. Thus the explant may be contacted with the adenoviral gene delivery vehicle within 1 hour of extraction from the donor, within 45 minutes, within 30 minutes, within 15 minutes, within 10 minutes, within 5 minutes or within 1 minute of extraction from the donor.

Alternatively, the cell or tissue may have been cultured in vitro for a period of time prior to contacting with the adenoviral gene delivery vehicle, e.g. for a period of one or more hours, days or weeks. The cell or tissue may have been generated in vitro, e.g. from one or more stem cells, by growth and differentiation under appropriate culture conditions. In such cases, the stem cells may be syngeneic with the subject to whom the cell or tissue is to be administered. For example, they may have been obtained directly or indirectly from the subject themselves. Alternatively they may have been obtained directly or indirectly from a third party donor.

The vascular cell or tissue may be contacted with the gene delivery vehicle for as long as necessary to achieve adequate transduction. Often, however, a period of one hour or less may suffice, e.g. 45 minutes or less, 30 minutes or less, 15 minutes or less, or 10 minutes or less. For example, the vascular cell or tissue may be contacted with the gene delivery vehicle for a period of 10 minutes to 1 hour, 15 minutes to one hour, 30 minutes to 1 hour, 45 minutes to 1 hour, 10 minutes to 45 minutes, 15 minutes to 45 minutes, 30 minutes to 45 minutes, 10 minutes to 30 minutes, 15 minutes to 30 minutes or 10 minutes to 15 minutes.

Where the vascular cell or tissue is an explant, the explant may be contacted with the gene delivery vehicle for the relevant period of time after extraction from the donor and prior to grafting into the recipient subject.

The objective of the surgical method as a whole may be prophylaxis or treatment of coronary artery disease (CAD). The method may comprise a step of vascular grafting. Thus the method may comprise a step of coronary artery bypass grafting (CABG) or percutaneous transluminal coronary angioplasty (PTCA).

The objective of gene transfer to the vascular cell or tissue may be, for example, vaccination or gene therapy.

Gene therapy applications may include modulation of angiogenesis or vasculogenesis, e.g. promotion of angiogenesis or vasculogenesis (i.e. therapeutic angiogenesis/vasculogenesis, e.g. for treatment of ischaemia) or inhibition of angiogenesis or vasculogenesis (in situations where angiogenesis or vasculogenesis is undesirable, e.g. in the treatment of cancers or inflammatory conditions), prophylaxis or treatment of peripheral vascular disease, prophylaxis or treatment of restenosis (such as in-stent restenosis), prophylaxis or treatment of complications resulting from vascular surgery (e.g. following CABG or PTCA as described above), prophylaxis or treatment of vein graft failure, modulation of vascular cell proliferation (e.g. inhibition of undesirable vascular cell proliferation such as neointimal hyperplasia), modulation (e.g. inhibition or stimulation) of vascular cell apoptosis, modulation (e.g. inhibition or stimulation) of vascular cell migration, or prophylaxis or treatment of atheroma formation, atherosclerosis or vascular occlusion.

It will be appreciated that these various applications are not necessarily mutually exclusive.

The site of intended treatment may be a vascular graft.

In a further aspect, the invention provides the use of an adenoviral gene delivery vehicle for gene delivery to a vascular cell or tissue, wherein the adenoviral gene delivery vehicle comprises an Ad49 major capsid protein.

In a further aspect, the invention provides an adenoviral gene delivery vehicle for gene delivery to a vascular cell or tissue, wherein the adenoviral gene delivery vehicle comprises an Ad49 major capsid protein.

In a further aspect, the invention provides an adenoviral gene delivery vehicle in the preparation of a medicament for use in gene delivery to a vascular cell or tissue, wherein the adenoviral gene delivery vehicle comprises an Ad49 major capsid protein.

It will be appreciated that features of the methods described above are equally applicable to these aspects of the invention.

In any of the above-described aspects of the invention, the adenoviral gene delivery vehicle may have an Ad49 hexon protein, penton protein, or fiber protein.

For example, it may have an Ad49 hexon protein and penton protein, an Ad49 hexon protein and fiber protein, or an Ad49 penton protein and fiber protein.

For example, it may have an Ad49 hexon protein, penton protein and fiber protein.

The adenoviral gene delivery vehicle may be chimeric, i.e. it may possess one or more major capsid proteins from one or more different adenoviral families or serotypes.

Especially when the gene delivery vehicle is to be used in vivo, it may be desirable that the capsid is composed of proteins to which the subject recipient has little or no pre-existing immunity. Apart from Ad49, suitable serotypes may include Ad11, Ad26, Ad34, Ad35, Ad48, Ad50 and simian adenoviruses. The gene delivery vehicle must retain sufficient Ad49 major capsid components to maintain tropism for vascular cells (compared to, for example, hepatocytes), but other capsid components may be derived from one or more serotypes other than Ad49, such as Ad35.

For example, the gene delivery vehicle may comprise;
Ad49 hexon protein, and penton and fiber proteins from one or more other serotypes;
Ad49 penton protein, and hexon and fiber proteins from one or more other serotypes;
Ad49 fiber protein, and penton and hexon proteins from one or more other serotypes;
Ad49 hexon and penton proteins, and fiber protein from one or more other serotypes;
Ad49 hexon and fiber proteins, and penton protein from one or more other serotypes; or
Ad49 penton and fiber proteins, and hexon protein from one or more other serotypes.

It may be desirable that the gene delivery vehicle contains Ad49 hexon protein.

It will be appreciated that any individual virion will typically not contain mixtures of any individual protein. That is to say, all hexon proteins in one virion will typically be of the same serotype, as will all of the penton and fiber proteins. However, this need not always be the case; in some circumstances it may be desirable that a virion contains more than one serotype of one or more proteins. Populations of virions may be homogeneous or heterogeneous in this regard.

The gene delivery vehicle carries a nucleic acid payload for delivery to the target cell or tissue. The nucleic acid payload is normally a double stranded DNA (dsDNA) molecule. The nucleic acid payload typically comprises a heterologous gene (i.e. a gene not found in wild type adenoviruses) which is intended for introduction into and expression in the target vascular cell or tissue. Thus the heterologous gene may be part of a transcription unit functional to express the heterologous gene in the target cell or tissue. Thus the heterologous gene may be operably linked to a promoter and other appropriate transcriptional and translational regulatory signals. The heterologous gene may also be referred to as a "transgene". Introduction of the nucleic acid payload and its heterologous gene into a target cell or tissue is referred to as "transduction".

The nucleic acid payload typically contains further elements required for it to be packaged into the adenoviral gene delivery vehicle and appropriately processed in the target vascular cell or tissue. These may include adenoviral inverted terminal repeat (ITR) sequences and an appropriate packaging signal.

The nucleic acid payload may also contain a selectable marker, i.e. a gene encoding a product which allows ready detection of transduced cells. Examples include genes for fluorescent proteins (e.g. GFP), enzymes which produce a visible reaction product (e.g. beta-galactosidase, luciferase) and antibiotic resistance genes.

The adenoviral gene delivery vehicle is typically not replication-competent. That is to say, the nucleic acid does not contain all of the adenoviral genes (and other genetic elements) necessary for viral replication. Typically the nucleic acid lacks one or more functional adenoviral genes from the E1, E2, E3 or E4 regions. These genes may be deleted or otherwise inactivated, e.g. by insertion of a transcription unit comprising the heterologous gene or a selective marker. In some embodiments, the nucleic acid contains no functional adenoviral genes, in which case the only viral components present may be the ITRs and packaging signal. Gene transfer vehicles having no functional adenoviral genes may be preferred, as they reduce the risk of a host immune response developing against the transduced target cell or tissue as a result of viral protein synthesis.

The heterologous gene is referred to herein as being "exogenous" to the target cell or tissue into which it is introduced. If the heterologous gene has no equivalent in the genome of the target cell or tissue, e.g. it encodes a product (RNA and/or protein) not already encoded by a gene in the target cell or tissue, then the exogenous gene may also be regarded as being heterologous to the target cell or tissue. The heterologous gene may encode any gene product which it is desirable to introduce to a vascular cell.

A number of types of genes are well known for use in methods of gene therapy, and include those encoding therapeutic proteins such as TPA, EPO, cytokines, antibodies or functional fragments or derivatives thereof, etc., as well as immunostimulatory factors like tumour-specific antigens, cytokines, etc.

The following examples of may be of particular interest for the present invention.

Anti-angiogenic factors such as endostatin, angiostatin, ATF-BPTI CDT-6, dominant negative VEGF-mutants, antibodies against VEGF, FGF, or functional fragments thereof, etc.

Pro-angiogenic (or vasculogenic) factors including VEGF (e.g. isoform 121, 159, 206 or 165), Fibroblast growth factors (FGFs, including FGF2, 3, 4 and 5), hepatocyte growth factor (HGF), IGF, del-1 (developmentally-regulated endothelial locus 1), Nitric oxide synthases (e.g. inducible NOS, also known as iNOS), C-type natriuretic peptide, etc. Many of these genes have been proposed in the literature as candidates for gene therapy approaches to angiogenesis and treatment of ischaemia. VEGF and nitric oxide synthases have been shown to be effective for inhibition of restenosis. VEGF may act via induction of nitric oxide synthase and/or prostacyclin, thus inhibiting VSMC proliferation and migration.

Anti-inflammatory proteins such as soluble CD40, FasL, IL-12, IL-10, IL-4, IL-13 and antibodies or functional fragments or derivatives thereof (e.g. secreted single chain antibodies) against CD4, CD5, CD7, CD52, Il-2, IL-1, IL-6, TNF, etc. or the T-cell receptor on auto-reactive T-cells. Dominant negative mutants of PML may also be used to inhibit the immune response.

Furthermore, antagonists of pro-inflammatory cytokines may be used, for example IL-lRA (receptor antagonist) and soluble receptors like siL-lRI, siL-lRII, sTNFRI and sTNFRII. Growth and/or immune response inhibiting genes such as ceNOS, Bcl3, cactus and IKBα, β or γ.

Genes encoding pro-apoptotic proteins like p53, metalloprotease inhibitors (e.g. TIMP 1-3) and the VP3 protein of chicken anemia virus may also be used. Furthermore, suicide genes like HSV-TK, cytosine deaminase, nitroreductase and linamerase may be used. p53 has been suggested for use in inducing apoptosis in SMCs to prevent neointimal hyperplasia in human saphenous vein grafts. TIMPs, such as TIMP 3, have been shown to inhibit neointimal hyperplasia by inducing SMC apoptosis, as well as by inhibiting migration of SMCs. TIMPs have also been shown to be effective for inhibition of restenosis.

Other genes encoding polypeptides effective to prevent or inhibit neointimal hyperplasia, atheroma formation, vascular occlusion or atherosclerosis are also of interest. These include regulators of vascular remodelling such as Nogo-B.

The heterologous gene may also encode a nucleic acid gene product, e.g. one capable of regulating expression of an endogenous gene in the target cell or tissue. Such regulatory nucleic acids include decoy oligodeoxynucleotides and nucleic acids capable of hybridising to mRNA or DNA of a target gene or inhibiting expression by co-suppression, such as ribozymes, antisense RNA or DNA molecules, siRNA, RNAi, etc. Regulatory nucleic acids (decoy oligodeoxynucleotides) directed against the transcription factor E2F have been shown to inhibit neointimal hyperplasia and vascular graft atherosclerosis in rabbits.

The invention will now be described in more detail, by way of example and not limitation, by reference to the accompanying drawings and examples.

DESCRIPTION OF THE DRAWINGS

FIG. 8: Ad49 hexon protein sequence (protein id= ABD52395.1; GI:88810182)

FIG. 9: Ad49 fiber protein sequence (protein id= ABD52400.1; GI:88810187)

FIG. 10: Ad49 penton protein sequence (protein id= ABD52391.1; GI:88810178)

DETAILED DESCRIPTION OF THE INVENTION

Adenoviruses and Adenoviral Vectors

Figure 1:
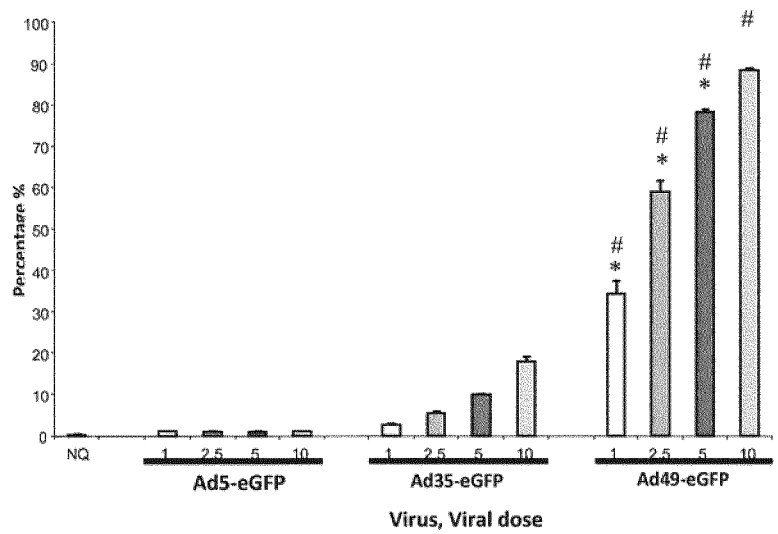
FIG. 1: Transduction dose response for Ad5, Ad35 and Ad49 in cultures of hSMC. Viruses were diluted to 1-10,000 vp/cell and incubated with cells for 3 hours. Cells were washed, and media replenished. Cells were visualised and photographed prior to FACS quantification of eGFP expression 48 hours post infection.

Adenoviruses are non-enveloped viruses containing a linear double-stranded DNA genome which infect various mammalian species including humans.

The genome is typically approximately 30-38 kp in length, and encodes a number of genes including so-called Early (E1a, E1b, E2a, E2b, E3, E4) and Late (L1, L2, L3, L4, L5) genes, flanked by 5' and 3' inverted terminal repeats (ITRs). It also contains a packaging signal.

The genome is enclosed in a capsid composed of three major proteins, namely penton, hexon, and fiber. The hexon is the most abundant structural component of the capsid (accounting for 63% of the total protein mass of the virus)[17] and is composed of 240 trimeric capsomeres. The other two proteins are the 12 pentameric penton bases and the fiber protein (which is a trimeric rod-like structure that projects from the 12 penton bases). The fiber contains a C-terminal globular knob-like structure that mediates primary cell tethering interactions. These proteins together form the icosahedral shape of the non-enveloped capsid (with a diameter of 70-90 cm) that surrounds a double stranded 36 kb DNA genome (reviewed in [20]).

The Ad fiber proteins are structured to interact with several different host cell receptors. The method for Ad infection in vitro is well defined, particularly for Ad5 (species C). Ads internalise into the host cells through endocytosis that is driven by the interaction of the cellular receptor of the host cell and the viral fiber protein and penton base. Initial interaction for most Ad species is between the fiber knob domain and the membrane glycoprotein coxsackievirus and adenovirus receptor (CAR). All Ad species except B can interact with CAR using the tight junction regulated fiber knob domain, although some species D Ads also use sialic acid. Species B Ads utilize CD46. Virus internalisation is stimulated through engagement of $\alpha_v\beta_3$ and $\alpha_v\beta_5$ integrins by the RGD motif in the penton base at the N-terminus of the fiber protein[21, 22].

Adenoviruses are frequently used as gene transfer vectors to deliver a nucleic acid payload to a target cell or tissue. The payload normally comprises or consists of a linear dsDNA molecule which in turn comprises a heterologous gene (often referred to as a transgene) which it is desired to introduce and express in the target cell or tissue.

The nucleic acid payload carried by such vectors generally lacks one or more genes essential for viral replication, especially one or more Early genes. The viral gene is typically deleted from the viral genome and replaced by the heterologous gene or genes. These vectors are thus replication-defective and are not capable of productive infection resulting in generation of viral progeny which are identical to the parent (unless the same cell is also infected with a helper virus capable of complementing the deficiency present in the vector genome).

Three generations of adenoviral vectors have been generated to date. The first generation lacked the E1 gene. The second generation combined deletion of E1 and/or E3 with deletions of E2 and/or E4. The third generation retains only the ITRs and packaging signal with the rest of the genome replaced by heterologous DNA, and are often called "gutless" or "gutted" vectors, or "helper-dependent adenoviruses" since they rely on a helper adenovirus to supply all viral proteins. See Alba et al. (Gene Ther. 8, 1347-1353, 2005) for a review. An overview of minimal vectors, packaging cells and ancillary techniques can also be found in WO99/55132 (PCT/NL00/00235).

For efficient packaging, the length of the nucleic acid payload is normally approximately 75-105% of the length of the wild type adenoviral genome appropriate to the capsid. The Ad49 genome is approximately 35.2 kb in length, so nucleic acid used in Ad49-based vectors will typically be approximately 26.5 to 37 kb in length.

The heterologous gene (and its transcription unit) will normally be shorter than the optimum length for packaging, so the remainder of the nucleic acid payload will be composed of so-called "stuffer" sequence. This is typically non-coding sequence (e.g. intron sequences) but without elements such as repetitive sequences, recombination hotspots and extraneous regulatory elements that could interfere with maintenance and expression of the heterologous gene.

Adenovirus Serotype 49

To date, six different subgroups of human adenoviruses have been proposed which in total encompass 55 distinct adenovirus serotypes. A serotype is defined on the basis of its immunological distinctiveness as determined by quantitative neutralization with animal antisera (horse, rabbit).

A serotype has either no cross-reaction with others, or shows a homologous-to-heterologous titer ratio of >16 in both directions. If neutralization shows a certain degree of cross-reaction between two viruses in either or both directions (homologous-to-heterologous titer ratio of 8 or 16), distinctiveness of serotype is assumed if (A) the hemagglutinins are unrelated, as shown by lack of cross-reaction on hemagglutination-inhibition, or (B) substantial biophysical/biochemical differences in DNA exist (Francki et al, 1991, Arch. Virol. Suppl. 2: 140-144).

A number of the most-recently identified serotypes were isolated for the first time from HIV-infected patients (e.g. Hierholzer et al., 1988, J. Infect. Dis. 158, 804-813; Schnurr et al 1993, Intervirol. 36, 79-83). For reasons not well understood, most of such immune-compromised patients shed adenoviruses that were rarely or never isolated from immune-competent individuals (Hierholzer et al 1988, J. Infect. Dis. 158, 804-813; De Jong et al, 1998, Lancet 1(8337): 1293-1296).

A whole genome sequence for adenovirus serotype 49 is provided in GenBank with the accession number DQ393829.1.

Example sequences for the major Ad49 capsid proteins are provided in FIGS. 8 (hexon), 9 (fiber) and 10 (penton).

The term "Ad49 hexon protein" is used herein to mean a hexon protein which shows the same pattern of serological reactivity with hexon proteins from other adenoviral serotypes as the hexon sequence provided in FIG. 8. Additionally or alternatively, an Ad49 hexon protein has the hexon sequence provided in FIG. 8 or a sequence having at least 93%, 94%, 95% 96%, 97%, 98%, or 99% identity to that sequence, or is a functional fragment of either.

The term "Ad49 fiber protein" is used herein to mean a fiber protein which shows the same pattern of serological reactivity with fiber proteins from other adenoviral serotypes as the fiber sequence provided in FIG. 9. Additionally or alternatively, an Ad49 fiber protein has the fiber sequence provided in FIG. 9 or a sequence having at least 80%, 81%, 82%, 83%, 84%, 85%, 86%, 87%, 88%, 89%, 90%, 91%, 92%, 93%, 94%, 95% 96%, 97%, 98%, or 99% identity to that sequence, or is a functional fragment of either.

The term "Ad49 penton protein" is used herein to mean a penton protein which shows the same pattern of serological reactivity with penton proteins from other adenoviral serotypes as the penton sequence provided in FIG. 10. Additionally or alternatively, an Ad49 penton protein has the penton sequence provided in FIG. 10 or a sequence having at least 98%, or 99% identity to that sequence, or is a functional fragment of either.

In particular, conservative substitutions in the hexon, fiber and penton sequence (as compared to the reference sequences provided) may be particularly well tolerated, without substantial effect on function.

A conservative substitution may be defined as a substitution within an amino acid class and/or a substitution that scores positive in the BLOSUM62 matrix.

According to one classification, the amino acid classes are acidic, basic, uncharged polar and nonpolar, wherein acidic amino acids are Asp and Glu; basic amino acids are Arg, Lys and His; uncharged polar amino acids are Asn, Gln, Ser, Thr and Tyr; and non-polar amino acids are Ala, Gly, Val, Leu, Ile, Pro, Phe, Met, Trp and Cys.

According to another classification, the amino acid classes are small hydrophilic, acid/acid amide/hydrophilic, basic, small hydrophobic and aromatic, wherein small hydrophilic amino acids are Ser, Thr, Pro, Ala and Gly; acid/acidamide/hydrophilic amino acids are Asn, Asp, Glu and Gln; basic amino acids are His, Arg and Lys; small hydrophobic amino acids are Met, Ile, Leu and Val; and aromatic amino acids are Phe, Tyr and Trp Substitutions which score positive in the BLOSUM62 matrix are as follows:

| | Original Residue | | | | | | | | | | | | | | | | | | |
|---|---|---|---|---|---|---|---|---|---|---|---|---|---|---|---|---|---|---|---|
| | C | S | T | P | A | G | N | D | E | Q | H | R | K | M | I | L | V | F | Y | W |
| Substitution | — | T | S | — | S | — | S | N | D | E | N | Q | E | I | M | M | M | Y | H | F |
| | | A | | | | | D | E | Q | R | Y | K | Q | L | L | I | I | W | F | Y |
| | | N | | | | | | | H | K | K | | | R | V | V | V | L | | W |

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined using the publically available alignment program MUSCLE (Edgar, 2004, Nucleic Acids Res. 32(5):1792-1797) using default parameters. A % amino acid sequence identity value is determined by the number of matching identical residues as determined by MUSCLE, divided by the total number of residues of the reference sequence (gaps introduced by the program into the reference sequence to maximize the alignment score being ignored), multiplied by 100.

The hexon protein, in combination with fiber proteins having the sequence of FIG. 9 and penton proteins having the sequence of FIG. 10, is capable of forming functional adenoviral virions capable of mediating vascular SMC or EC transduction at 50% or more (and preferably 60%, 70%, 75%. 80%, 85%, 90% or 95% or more) of the level provided by that of an otherwise identical gene transfer vehicle having a capsid composed of hexon, fiber and penton proteins having the sequences shown in FIGS. 8 to 10 respectively.

The fiber protein, in combination with hexon proteins having the sequence of FIG. 8 and penton proteins having the sequence of FIG. 10, is capable of forming functional adenoviral virions capable of mediating vascular SMC or EC transduction at 50% or more (and preferably 60%, 70%, 75%. 80%, 85%, 90% or 95% or more) of the level provided by that of an otherwise identical gene transfer vehicle having a capsid composed of hexon, fiber and penton proteins having the sequences shown in FIGS. 8 to 10 respectively.

The penton protein, in combination with hexon proteins having the sequence of FIG. 8 and fiber proteins having the sequence of FIG. 9, is capable of forming functional adenoviral virions capable of mediating vascular SMC or EC transduction at 50% or more (and preferably 60%, 70%, 75%. 80%, 85%, 90% or 95% or more) of the level provided by that of an otherwise identical gene transfer vehicle having a capsid composed of hexon, fiber and penton proteins having the sequences shown in FIGS. 8 to 10 respectively.

In each case, the level of transduction can be determined using primary human vascular SMCs in serum free medium, 37° C., at 2×10⁴ cells per well in a 96 well plate format. Cells are incubated with 10⁴ virus particles per cell for 30 minutes, before being washed with PBS. The cells are then maintained under the original conditions (serum free medium, 37° C.) for 48 hours before determining the level of transduction.

The level of transduction can be determined by measuring the level of expression of the transgene, normalised appropriately to cell number or total protein in the well. Expression may be assessed directly (as absolute protein concentration) or indirectly, e.g. via enzymatic activity.

A suitable transgene for use in the assay is luciferase, which may be expressed under the control of the CMV (cytomegalovirus) promoter. Luciferase assays measure intensity of light produced by action of the enzyme on a luciferin substrate in the presence of ATP-$Mg^{2+}$. The skilled person is well aware of suitable protocols for such determination, and the precise protocol used is not important. Examples include the Luciferase Assay System commercially available from Promega®.

The gene transfer vehicle may comprise other adenoviral proteins as appropriate, including minor capsid proteins, enzymes, etc. By way of illustration only, other Ad49 proteins have the following GenBank accession numbers (although the skilled person will be well capable of creating viral vectors having different proteins if desired):
pIX (ABD52385.1; GI:88810172)
pIVa2 (ABD52386.1; GI:88810173)
DNA polymerase (ABD52387.1; GI:88810174)
pTP: ABD52388.1; GI:88810175;
52/55K: ABD52389.1; GI:88810176;
pIIIa: ABD52390.1; GI:88810177;
pVII: ABD52392.1; GI:88810179;
pV: ABD52393.1; GI:88810180;
pVI: ABD52394.1; GI:88810181;
proteinase: ABD52396.1; GI:88810183;
DNA Binding Protein: ABD52397.1; GI:88810184;
100K: ABD52398.1; GI:88810185;
pVIII: ABD52399.1; GI:88810186.

In certain embodiments, the gene delivery vehicle comprises an E4-orf6 gene from adenovirus serotype 5. This allows propagation of E1-deleted Ad49 viruses in commonly-used Ad5-E1-complementing cell lines, such as HEK293 or PER.C6 cells. See, for example, WO03/104467, and Lemckert et al., (2006)[28]., which also provide further details regarding the production of vectors based on Ad49. In other embodiments an E1-deleted Ad49 virus does not comprise E4-orf6 of Ad5, in which case the vector can be complemented in a cell line that expresses both E1 and a compatible E4orf6, e.g. the 293-ORF6 cell line that expresses both E1 and E4orf6 from Ad5 (see e.g. Brough et al, 1996, *J Virol* 70: 6497-501 describing the generation of the 293-ORF6 cells; Abrahamsen et al, 1997, *J Virol* 71: 8946-51 and Nan et al, 2003, *Gene Therapy* 10: 326-36 each describing generation of E1 deleted non-subgroup C adenoviral vectors using such a cell line), or a complementing cell that expresses E1 from Ad49 can be used (see e.g. WO 00/70071, WO 02/40665).

Gene Therapy for Cardiovascular Disease

Cardiovascular diseases (CVD), including coronary artery diseases (CAD), are the leading cause of death in the developed world. Globally, about 17.1 million people die each year due to CVD reflecting 29% of all deaths. It is also estimated that the rate will increase reaching 23.6 million by 2030.[1]

The pathophysiological process of CAD begins with the narrowing of the coronary artery as a consequence of the presence of an atherosclerotic plaque within its lumen; the plaque may rupture due to inflammatory activity within it, resulting in acute thrombosis.[2] As a consequence, ischemic heart disease (IHD) can manifest, which is a condition in which the cardiac muscle is damaged and is then unable to perform efficiently due to the reduction of blood supply to the heart itself, leading to myocardial infarction (MI) and heart failure.[3]

The main surgical intervention methods used to relieve CAD symptoms are coronary artery bypass grafting (CABG) and percutaneous transluminal coronary angioplasty (PTCA). In CABG, the saphenous vein from the leg of the patient is used as the grafting blood vessel in the procedure, but a major limitation to it is that the symptoms reappear in up to 50% of cases within 10 years of the operation and repeated interventional surgery is then needed[4, 6], ultimately leading to a higher risk of obstruction with each repeated bypass surgery[7].

Arterial sources as grafting vessels have also been used in CABG, such as the left internal mammary artery (LIMA), radial artery, the right gastroepiploic artery, and the inferior epigastric artery,[4, 8] but the use of arterial sources for grafting has its own limitations, such as the increase in the duration and technical difficulty of the operation, the short length of the blood vessels available for grafting, as well as the possible occurrence of arterial spasm, especially when using the radial artery as a graft[4]. These procedures tend to be used more in younger patients who have a longer life expectancy[9]. Other surgical intervention methods used to treat CAD include PTCA (also known as balloon angioplasty) and stenting (the use of an expandable metal tube in order to keep the blocked artery open after angioplasty). However these methods also suffer from marked re-narrowing of the blood vessels after the procedure due to restenosis[10].

Vascular smooth muscle cells (VSMC) form the medial layer of the blood vessels and have the ability to remodel their phenotype in response to changes in their local environment, such as blood flow, stress on the inner lumen of the saphenous vein used in CABG, and injuries such as those caused by balloon PTCA. These changes cause the VSMC to shift from a differentiated state to a de-differentiated state and this modulation ends with the formation of neointimal lesions[6, 11, 12].

Neointimal hyperplasia is caused by the migration and proliferation of VSMC from the medial to the intimal layer of the vasculature and causes the vein graft to be susceptible to accelerated atherosclerosis[13]. This process is induced by cytokines and growth factors that are released from injured endothelial and smooth muscle cells, aggregating platelets, and macrophages[14, 15]. In that sense, the inhibition of neointimal formation at an early stage is important for the prevention of vein graft occlusion and atheroma formation.

In order to prevent neointimal lesion formation and prolong the life span of vein grafts, therapeutic gene transfer into the wall of vein grafts might have the potential to prevent late graft failure. Vein grafts are considered to be perfect targets for gene therapy owing to the fact that explanted veins can be transduced ex vivo before the actual grafting process, thus avoiding the numerous limitations and difficulties associated with in vivo gene transfer.

Metalloproteinases (MMPs) induce vascular SMC migration and proliferation that leads to vascular neointimal formation in late vein grafting failure. George et al have shown that over expressing tissue inhibitor of metalloproteinase-3 (TIMP-3) has a regulatory effect on MMPs by blocking its effect and inducing VSMC apoptosis[23].

Inducing VSMC apoptosis by overexpressing the tumour suppressor gene p53 has also been investigated in order to regulate VSMC migration and proliferation, thus leading to a reduced intimal thickening and of intimal cell number [24]. Another method of reducing neointimal formation is over expressing the protein Nogo-B which is believed to be a regulator of vascular remodelling. Nogo-B is lost following vascular injury, and by over-expressing it a reduction in proliferation and migration of the VSMC was seen in porcine and murine neointimal models[25].

Examples

Materials and Methods

Cell Cultures

Smooth muscle cells and endothelial cells were prepared from human saphenous vein segments that were obtained from patients undergoing coronary artery bypass grafting at Clydebank Hospital, who gave informed consent. Ethical permission was obtained from the West Glasgow Ethics Committee.

Human Saphenous Vein Endothelial cells (HSVEC) and Smooth Muscle Cells (HSVSMC) are obtained and grown from medial explants of the human saphenous vein and were maintained in endothelial cell complete media (TCS Cell Works, UK) supplemented with 20% foetal calf serum (FCS; PAA laboratories, UK) and Dulbecco's modified Eagle's medium (DMEM) with 4500 mg/l glucose supplemented with 20% FCS and 100 IU/ml penicillin, 100 µg/ml streptomycin and 2 mM/1 L-Glutamine respectively.

Human embryonic kidney HEK293 cells and HepG2 cells were cultured in minimal essential medium supplemented with 100 IU/mL penicillin, 100 mg/mL streptomycin, 2 mmol/L L-glutamine (Invitrogen), 10% (vol/vol) FCS (FCS; PAA Laboratories) and 1 mM sodium pyruvate (Sigma-Aldrich).

Cells were cultured as a monolayer and media was replaced every 3-4 days. Cells were routinely maintained at approximately 80% confluence to prevent overgrowth and loss of surface contact. In the passage process, cells were washed in 10 ml PBS and were incubated in 3 ml of TE (trypsin-EDTA, Gibco, Paisley, UK) for approximately 3 minutes at 37° C. until the detachment of the cells from the flask. After that, 5 ml of complete media was added in order to counteract the effect of TE. Cells were collected by configuration at 1500 rpm for 5 minutes and then were resuspended in complete media for passaging or seeding. Before seeding cells were counted using a haemocytometer to make sure of the required seeding density.

FACS Analysis of Adenoviral Receptors on hSMCs

Expression levels of the primary adenoviral receptors CAR, CD46 and Desmoglein 2, as well as the coreceptors $\alpha v\beta 3$ and $\alpha v\beta 5$ was evaluated by FACS. Briefly, $1\times 10^5$ hSMC cells were washed in PBS and resuspended in serum free media containing either 1:500 dilution of relevant antibody (RmcB (mouse monoclonal anti-CAR), MEM-258 (mouse monoclonal anti-CD46), 6D8 (mouse monoclonal anti-DSG-2), LM609 (mouse monoclonal anti-$\alpha v\beta 3$), P1F6 (mouse monoclonal anti-$\alpha v\beta 5$) or mouse IgG control for 1 hour on ice. After 1 hour, the cells were pelleted, washed, and resuspended in alexa-488 labelled rabbit anti mouse secondary antibody for 1 hour on ice. Finally cells were pelleted again, washed in PBS, and resuspended in serum free media and analyses on a BD FACS Canto 2. Cells were gated such that negative control (IgG stained cells) stained less than 1% positive.

In Vitro Cell Transduction Assays

Transduction experiments were performed in a 96 well-format with $2\times 10^4$ hSMCs per well. Cells were infected with adenoviruses at a doses ranging from 1000 to 10000 VP/cell depending on the experiment (see legend) in serum-free medium. Cells were infected for time periods ranging from 10 minutes-3 hours depending on the experiment (see separate figure legends) at 37° C., washed with PBS, and maintained until harvesting 48 hours post-infection. In some experiments, cells were blocked (on ice for 1 hour) using either 5 µg/$10^5$ cells of recombinant Ad5 knob protein (to block CAR receptors) or 2.5 µg/ml of CD46 blocking MEM258 antibody. In these experiments, the blocking agent was left on the cells for an additional hour in the presence of adenovirus (100 vp/cell) on ice for 1 hour, before the virus/blocking agent was removed from the cells, the cells washed in cold PBS and cultured for a further 48 hours in complete media prior to assay for luciferase expression. Luciferase activity was quantified using luciferase assay reagent (Promega) according to manufacturer's instructions. In some experiments where adenovirus expressing eGFP was used, cells were imaged using a fluorescence microscope, and the percentage cells positive for eGFP was quantified using a BD FACS Canto. Luciferase activity was quantified using a Wallac VICTOR2 luminometer (Perkin Elmer Life and Analytical Sciences, Boston, Mass., USA). Protein concentrations were calculated using a BCA assay (Thermo Scientific, Winsford, United Kingdom). Values are expressed as relative light units (RLU) per milligram of protein.

Serum Neutralisation Studies

To assess levels of preexisiting immunity against Ad5, Ad49 and Ad35, A549 cells were infected with 10000 vp/cell of luciferase expressing forms of each vector in the presence or absence of 2.5% sera from patients undergoing CABG within a Glasgow cohort. Luciferase expression was gauged as described earlier, and normalised to protein. The % change in transduction compared to no serum control was calculated, and serums which reduced transduction by greater than 90% were considered as highly neutralising.

Production and Purification of Recombinant Adenoviral Knob Proteins

The Ad49 knob sequence (generated by geneART with Ad5 hinge region and 6×HIS tag) or Ad5 knob sequence was cloned into pQE inducible expression vector. Protein production induced with IPTG and purified by affinity chromatography and eluted with increasing concentrations of imidizole. The capacity of the knob protein to trimerise was confirmed by running the purified protein under naturing or denaturing conditions. The trimeric protein was then used in transduction assays to compete out Ad5 or Ad49 mediated transduction as described earlier.

Ex Vivo Transduction Assays in Murine, Porcine and Human Vessels

Samples of murine (aorta), porcine (saphenous) and human (internal mammary) vessels were trimmed to remove adventitial tissue, cut into approximately equally sized pieces, washed in PBS, and infected with $10^9$ or $10^{10}$ vp of Ad5 or Ad49 expressing luciferase for time periods ranging from 10 minutes-3 hours depending on the experiment (standard being 1 hour) in serum free media. 48 hours post infection, samples were soaked in D-Luciferin, and imaged using a IVIS Spectrum.

Results
Evaluation of Adenoviral Receptor Expression on Cultures of Human Smooth Muscle Cells (hSMCs) and Human Endothelial Cells (hECs)

FACS analysis was employed to ascertain the levels of expression of known adenoviral receptors on hSMCs and hECs, with relevant isotype matched controls (Table 1). Expression of the species C Ad5 receptor (CAR) was found to be surprisingly low on both cell types, whilst the species B receptor (CD46) was found to be substantially higher. Furthermore we have quantified the expression of desmoglein-2 (DSG-2) the recently identified primary receptor for the species B adenoviruses Ad3, 7, 11 and 14, as well as other receptors and co-receptors. We observed low levels of DSG-2 expression, and moderate levels of integrins.

TABLE 1

Receptor and co-receptor expression on SMC and in EC.

| Receptor expressed | Percentage | |
|---|---|---|
| | hSMC | hEC |
| CD46 | 68.7% | 98% |
| CAR | 1.8% | 2.4% |
| DSG-2 | 3.3% | 2.2% |
| αvβ5 | 47.7% | 55.7% |
| αvβ5 | 62.5% | 93.1% |

Low level of expression of the primary Ad5 receptor CAR on hSMCs and hECs will significantly limit transduction efficacy, necessitating extremely high doses for efficient gene transfer. Vectors based on CD46 binding, or other undefined highly expressed receptors present on these cell types, will be more efficient for therapeutic gene transfer to vascular cells.

Assessing the Potential of Alternative Ad Serotypes for Vascular Gene Transfer.

We performed transduction assays in cultures of primary vascular hSMCs and ECs using luciferase-expressing adenoviral vectors based on Ad5, Ad26, Ad35, Ad48, Ad49 and Ad50.

Based on our preliminary findings (not shown), we pursued studies with Ad5, Ad35 and Ad49. A dose response experiment (1-10,000 vp/cell) was performed in hSMCs. 48 hours post infection, the cells were visualized and photographed (not shown) and the % cell positive for eGFP expression was quantified by FACS (see FIG. 1).

The CD46-utilising Ad35 is able to mediate significantly higher levels of transduction in hSMCs when compared with Ad5. Ad49, for which the receptor usage is unknown, shows significantly higher levels of transduction than Ad5 or Ad35 at all doses tested. Ad49 was also found to be capable of transducing vascular endothelial cells (data not shown).

Evaluating Transduction in hSMC Cultures Following Limited Duration Exposure to Ad.

Figure 2:
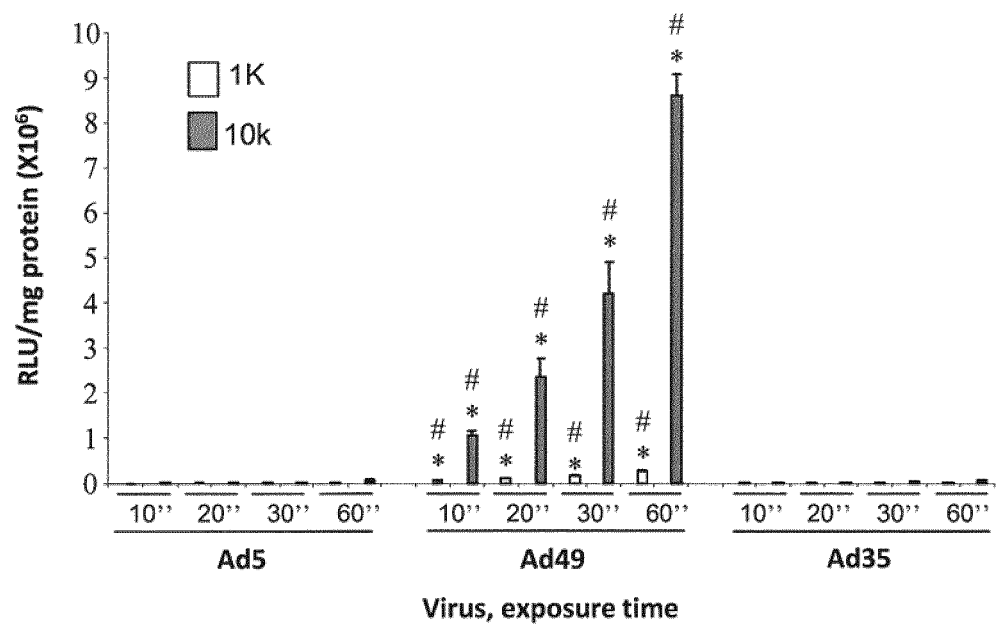
FIG. 2: Effect of limited exposure period of Ad5, Ad35 and Ad49 on transgene expression in hSMCs. hSMC were transduced with 1 k or 10 k/cell of Ad5, Ad35 or Ad49 for 10-60 minutes. Luciferase expression was quantified 48 hours later. * $p<0.0001$ vs Ad5, # $p<0.0001$ vs Ad35.

The procedure of bypass grafting offers a clinical window of ~30 minutes in order to perform ex vivo gene transfer to the vessel before re-introduction of the graft to the patient. Hence it is important that the selected gene therapy agent can deliver its DNA payload within this clinical window. Therefore we incubated primary cultures of hSMCs with either 1000 or 10000 vp/cell of Ad5, Ad35 or Ad49 for time periods of 10-60 minutes, and assessed levels of luciferase activity 48 hours post infection (FIG. 2). Ad49 mediated significantly and substantially higher levels of transgene expression in hSMCs than Ad5 and Ad35 at both doses tested and across all exposure time points assessed.

Ad49 mediates highly efficient transduction in hSMCs even following limited contact time with the target cells.

Evaluating Levels of Preexisting Immunity Against Ad5, Ad35 and Ad49

Figure 3:
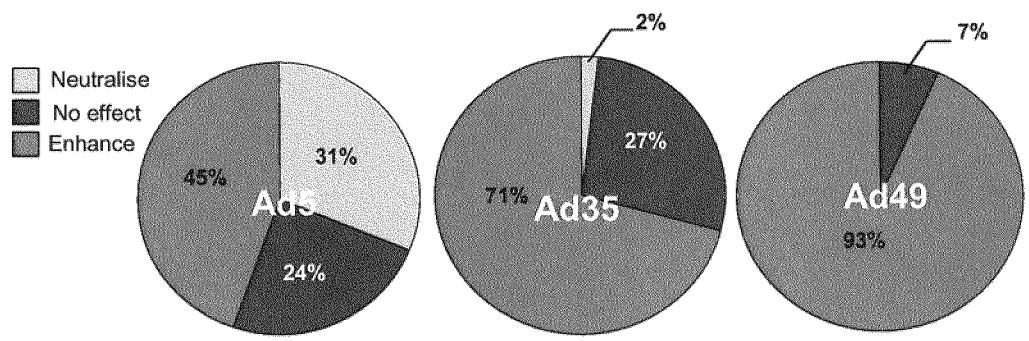
FIG. 3: Effect of neutralising serum on Ad mediated transduction of HepG2 cells. Cells were infected with 10 k vp/cell, and in the presence or absence of neutralising serum derived from patients undergoing CABG (103 samples total). The effect on transduction was gauged 48 hours post infection, with neutralisation taken as the capacity to reduce Ad mediated luciferase expression by greater than 90%.

Pre-existing anti vector immunity acquired through previous exposure to the wild type pathogens may limit clinical efficacy of these virus based gene therapy agents. To assess levels of pre-existing immunity against these vectors, we performed transduction assays by incubating luciferase expressing Ad5, Ad35 and Ad49 and incubating them with 2.5% serum from patients undergoing CABG procedure (Scottish cohort) prior to infecting HepG2 cells (20,000 cells/well, 10,000 vp/cell). The effect of serum on Ad mediated luciferase expression was quantified 48 hours post infection. Sera were categorised into 3 groups: neutralising (i.e. reduced luciferase expression by greater than 90% vs no serum control), no effect luciferase expression (i.e. 10-100% no serum control) or enhancing (i.e. luciferase expression was greater than 100% that of the no serum control) (FIG. 3).

Both Ad35 and Ad49 (in particular) demonstrated much lower level of pre-existing anti-vector immunity in the Scottish community than Ad5.

Effect of Ad49 Fiber Knob Protein on Blocking Ad49 Mediated Transduction.

Figure 4:
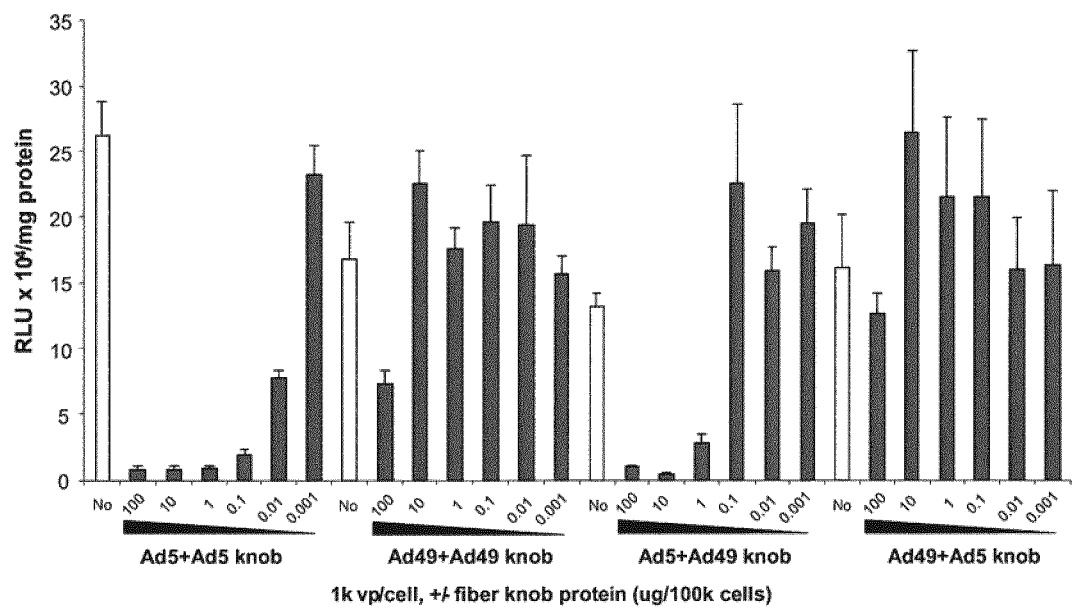
FIG. 4: Effect of Ad49 knob protein on Ad5 and Ad49 infectivity. The effect of Ad49 knob and Ad5 knob on Ad49 and Ad5 infectivity was quantified by incubating cells with a range of doses of knob protein and subsequently establishing the effects on transduction.

We sought to establish whether cellular infectivity of Ad49 is mediated via fiber knob interactions. We therefore cloned the Ad49 knob sequence (generated by geneART with Ad5 hinge region and 6×HIS tag) into pQE inducible expression vector. Protein production was induced with IPTG and the protein purified by affinity chromatography and eluted with increasing concentrations of imidizole. We confirmed that the recombinant protein trimerises (data not shown). We then studied the effect of recombinant Ad5 and Ad49 knob proteins using 100 µg/$10^5$ cells-0.001 µg/$10^5$ cells on transduction of either Ad5 or Ad49. Ad5 knob protein efficient and dose dependently inhibited transduction mediated by Ad5, but had no effect on Ad49 transduction. Intriguingly, Ad49 knob protein had no effect on Ad49 transduction, however it was able to inhibit CAR mediated Ad5 infectivity, albeit at 1-2 logs higher dose than Ad5 knob protein (FIG. 4).

These data suggest the Ad49 knob protein binds CAR and blocks CAR mediated Ad5 infectivity (albeit 1-2 logs lower affinity than Ad5 knob), but fails to block infectivity of Ad49, suggesting that Ad49 transduction is independent of knob interactions.

Ex Vivo Transduction of Mouse Aorta Using Ad5 and Ad49

Figure 5:
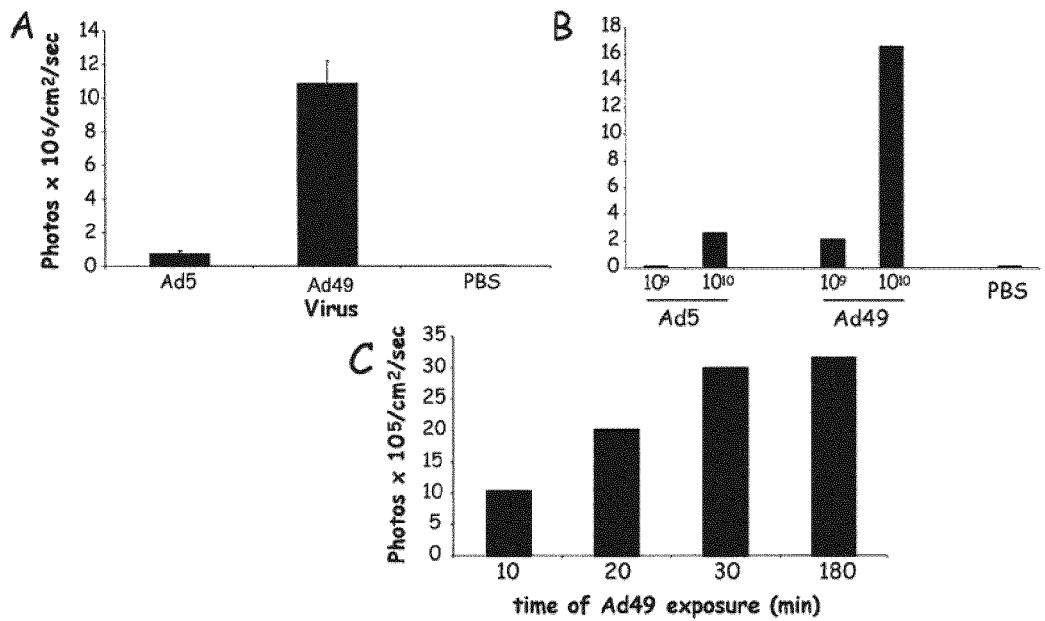
FIG. 5: Ex vivo transduction of mouse aorta using Ad5 or Ad49. Aorta were surgically isolated from C57/b6 mice and divided into equally sized section, before being exposed to either Ad5, Ad49 (both expressing luciferase) or PBS at a dose of $10^9$ vp/vessel (panels A and C) or $10^9$ and $10^{10}$ vp/vessel (panel B) for 1 hour at 37° C. (except for C, where the exposure period was varied from 10-180 minutes). Vessels were soaked in D-luciferin and imaged using an IVIS spectrum.

To ascertain the potential of Ad49 as an agent for mediating efficient gene transfer to the vasculature in clinical bypass grafting, we isolated aortas from C57 mice, cut them into 3 equally sized sections and then treated each piece ex vivo by dipping them into a solution of $10^9$ vp of either Ad5-Luc, Ad49-Luc or PBS for 1 hour at 37° C., before media was removed and the vessel cultured for a further 2 days in complete media. The resultant luciferase expression was quantified using by soaking the vessel in D-luciferin and imaging using an IVIS (FIG. 5A). Ad49 was found to mediate significantly higher levels of gene expression than Ad5. This experiment was repeated using 2 doses of Ad5 and Ad49, $10^9$ vp/vessel and $10^{10}$ vp/vessel (FIG. 5B). Finally we performed a time course experiment using $10^9$ vp of Ad49-Luc and exposed the vessel to the virus for 10-180 minutes (FIG. 5C).

These data suggest that Ad49 is significantly more efficient at transducing vasculature ex vivo than Ad5, and that Ad49 uptake and transduction occurs within a rapid, clinically relevant window.

Ex Vivo Transduction of Pig Saphenous Vein Using Ad5 and Ad49

Figure 6:
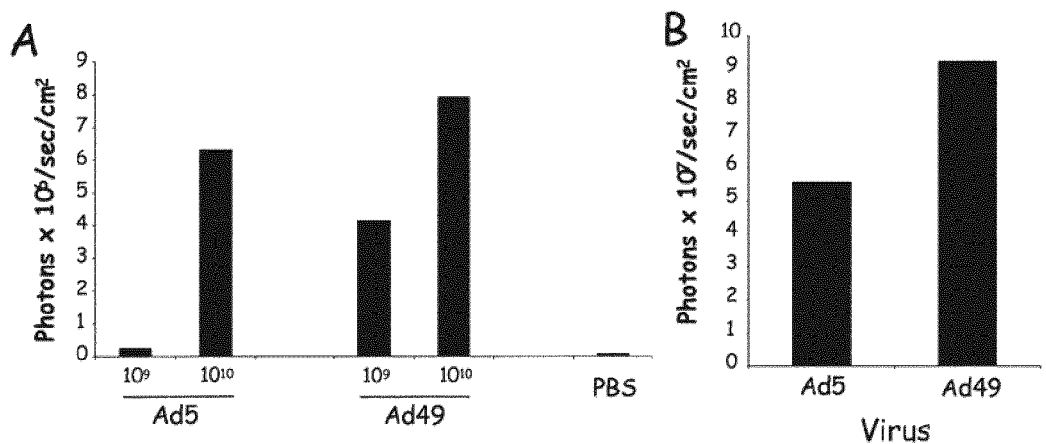
FIG. 6: Ex vivo transduction of pig saphenous vein using Ad5 or Ad49. Pig saphenous veins were divided into equally sized section, before being exposed to either Ad5, Ad49 (expressing luciferase) or PBS at a dose of $10^9$ or $10^{10}$ vp/vessel for 1 hour at 37° C. (A). $1\times10^{11}$ vp of Ad5 or Ad49 was introduced into the lumen of a pig saphenous vein and incubated for 1 hour at 37° C. (Figure B). Vessels were soaked in D-luciferin and imaged using an IVIS spectrum 48 hours post infection.

To extend the studies outlined above using a preclinical large animal model, we isolated spare saphenous veins from pigs and transduced the vessels as above with $10^9$ or $10^{10}$ vp of Ad5 or Ad49. We noted higher levels of transduction in vessels treated with Ad49 compared to Ad5, particularly at the lower dose tested (FIG. 6A). Furthermore we performed luminal dwell experiments, whereby $10^{11}$ vp of either Ad5 or Ad49 were introduced into the lumen of a pig saphenous vein (FIG. 6B). After 1 hour incubation, the vessel was washed with PBS and cultured for a further 48 hours prior to quantification of luciferase expression using IVIS.

These data suggest that Ad49 can efficiently transduce pig vasculature in ex vivo procedures, and is more efficient than Ad5 especially at lower doses. Since our data suggests that the pig isoform of CD46 is sufficiently different to the human form to prevent transduction with species B adenoviruses (e.g. Ad35) this also provides additional evidence that the receptor(s) utilized by Ad49 is not CD46.

Ex Vivo Transduction of Human Internal Mammary Artery Using Ad5 and Ad49

Figure 7:
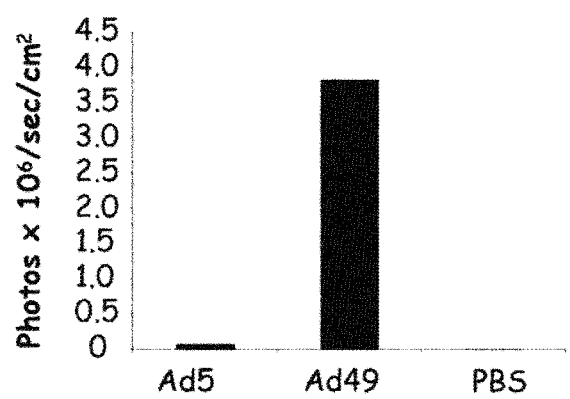
FIG. 7: Ex vivo transduction of human internal mammary artery using Ad5 or Ad49. Excess clinical material from a coronary bypass grafting procedure was cut into equally sized sections, before being exposed to either Ad5, Ad49 or PBS at a dose of $10^9$ vp/vessel. Vessels were soaked in D-luciferin and imaged using an IVIS spectrum.

To evaluate the efficiency with which Ad49 could transduce vascular cells from excess tissue from bypass graft operations, we performed ex vivo transduction of a section of internal mammary artery using $10^9$ vp of Ad5 or Ad49 as described in the preceeding sections. As depicted in FIG. 7, Ad49 mediated higher levels of transgene expression in the vessel (~25× higher) compared to Ad5 at the same dose.

Ad49 is highly efficient at transducing human vascular tissue ex vivo.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

REFERENCES

1. World Health Organisation. Cardiovascular Diseases. Last viewed 7 Jun. 2011. (http://www.who.int/mediacentre/factsheets/fs317/en/index.html).
2. M. J. Davies, Pathophysiology of acute coronary syndromes. Indian Heart J 52, 473 (2000).
3. P. Libby, P. Theroux, Pathophysiology of coronary artery disease. Circulation 111, 3481 (2005).
4. E. F. Akowuah, P. J. Sheridan, G. J. Cooper, C. Newman, Preventing saphenous vein graft failure: Does gene therapy have a role? Annals of Thoracic Surgery 76, 959 (2003).
5. A.D.A.M Images and medical illustrations. Last viewed 7 Jun. 2011. (http://www.adamimages.com/).
6. P. Turunen et al., Extracellular superoxide dismutase with vaccinia virus anti-inflammatory protein 35K or tissue inhibitor of metalloproteinase-1: Combination gene therapy in the treatment of vein graft stenosis in rabbits. Human Gene Therapy 17, 405 (2006).
7. M. Carlino et al., Prevention of distal embolization during saphenous vein graft lesion angioplasty—Experience with a new temporary occlusion and aspiration system. Circulation 99, 3221 (1999).
8. C. Purcell, M. Tennant, J. McGeachie, Neo-intimal hyperplasia in vascular grafts and its implications for autologous arterial grafting. Annals of the Royal College of Surgeons of England 79, 164 (1997).
9. S. Kitamura et al., Excellent Patency And Growth-Potential Of Internal Mammary Artery Grafts In Pediatric Coronary-Artery Bypass-Surgery—New Evidence For A Live Conduit. Circulation 78, 129 (1988).
10. N. Grabow, D. P. Martin, K. P. Schmitz, K. Sternberg, Absorbable polymer stent technologies for vascular regeneration. Journal of Chemical Technology and Biotechnology 85, 744 (2010).
11. G. K. Owens, M. S. Kumar, B. R. Wamhoff, Molecular regulation of vascular smooth muscle cell differentiation in development and disease. Physiological Reviews 84, 767 (2004).
12. Y. H. Cheng et al., MicroRNA-145, a Novel Smooth Muscle Cell Phenotypic Marker and Modulator, Controls Vascular Neointimal Lesion Formation. Circulation Research 105, 158 (2009).
13. A. C. Newby, A. B. Zaltsman, Molecular mechanisms in intimal hyperplasia. Journal of Pathology 190, 300 (2000).
14. J. J. Fuster et al., Control of cell proliferation in atherosclerosis: insights from animal models and human studies. Cardiovascular Research 86, 254 (2010).
15. M. M. Gaffney, S. O. Hynes, F. Barry, T. O'Brien, Cardiovascular gene therapy: current status and therapeutic potential. British Journal of Pharmacology 152, 175 (2007).
16. X. Danthinne, M. J. Imperiale, Production of first generation adenovirus vectors: a review. Gene Therapy 7, 1707 (2000).
17. J. J. Rux, R. M. Burnett, Adenovirus structure. Human Gene Therapy 15, 1167 (2004).
18. L. S. Young, P. F. Searle, D. Onion, V. Mautner, Viral gene therapy strategies: from basic science to clinical application. Journal of Pathology 208, 299 (2006).
19. S. E. Raper et al., Fatal systemic inflammatory response syndrome in a ornithine transcarbamylase deficient patient following adenoviral gene transfer. Molecular Genetics and Metabolism 80, 148 (2003).
20. S. A. Nicklin, E. Wu, G. R. Nemerow, A. H. Baker, The influence of adenovirus fiber structure and function on vector development for gene therapy. Molecular Therapy 12, 384 (2005).
21. J. Howitt, M. C. Bewley, V. Graziano, J. M. Flanagan, P. Freimuth, Structural basis for variation in adenovirus affinity for the cellular coxsackievirus and adenovirus receptor. Journal of Biological Chemistry 278, 26208 (2003).
22. N. Arnberg, Adenovirus receptors: implications for tropism, treatment and targeting. Reviews in Medical Virology 19, 165 (2009).
23. George, S. J., et al. (2000), 'Inhibition of late vein graft neointima formation in human and porcine models by adenovirus-mediated overexpression of tissue inhibitor of metalloproteinase-3', Circulation, 101 (3), 296-304.
24. George, S. J., et al. (2001), 'Wild-type p53 gene transfer inhibits neointima formation in human saphenous vein by modulation of smooth muscle cell migration and induction of apoptosis', *Gene Therapy*, 8 (9), 668-76.
25. Kritz, A. B., et al. (2008), 'In Vivo Modulation of Nogo-B Attenuates Neointima Formation', *Molecular Therapy*, 16 (11), 1798-804.
26. D. Schnurr, M. E. Dondero, 2 NEW CANDIDATE ADENOVIRUS SEROTYPES. Intervirology 36, 79 (1993).
27. D. Schnurr, A. Bollen, L. Crawfordmiksza, M. E. Dondero, S. Yagi, ADENOVIRUS MIXTURE ISOLATED FROM THE BRAIN OF AN AIDS PATIENT WITH ENCEPHALITIS. Journal of Medical Virology 47, 168 (1995).
28. A. A. C. Lemckert et al., Generation of a novel replication-incompetent adenoviral vector derived from human adenovirus type 49: manufacture on PER.C6 cells, tropism and immunogenicity. Journal of General Virology 87, 2891 (2006).
29. A. R. Thorner et al., Age dependence of adenovirus-specific neutralizing antibody titers in individuals from sub-Saharan Africa. Journal of Clinical Microbiology 44, 3781 (2006).
30. P. Abbink et al., Comparative seroprevalence and immunogenicity of six rare serotype recombinant adenovirus vaccine vectors from subgroups B and D. Journal of Virology 81, 4654 (2007).

The invention claimed is:

1. A method of gene delivery or gene transfer to a vascular cell or tissue comprising contacting said vascular cell or tissue with an adenoviral gene delivery vehicle, wherein the adenoviral gene delivery vehicle comprises an Ad49 hexon protein, an Ad49 penton protein, an Ad49 fiber protein, and a nucleic acid payload comprising a heterologous gene, thereby providing a genetically modified cell or tissue.

2. The method according to claim 1, wherein the method is performed in vitro or ex vitro.

3. The method according to claim 2, wherein the genetically modified vascular cell or tissue is intended for introduction to a subject.

4. The method according to claim 1 further comprising introducing the genetically modified cell or tissue into a subject.

5. The method according to claim 1, wherein the vascular cell or tissue comprises a length of blood vessel.

6. The method according to claim 5, wherein the length of blood vessel is derived from saphenous vein, internal mammary artery, gastroepiploic artery, or inferior epigastric artery.

7. The method according to claim 4, wherein the gene transfer or gene delivery is performed for modulation of angiogenesis or vasculogenesis, prophylaxis or treatment of peripheral vascular disease, prophylaxis or treatment of restenosis, prophylaxis or treatment of complications resulting from vascular surgery, prophylaxis or treatment of vein graft failure, modulation of vascular cell proliferation, modulation of vascular cell apoptosis, modulation of vascular cell migration, or prophylaxis or treatment of atheroma formation, atherosclerosis or vascular occlusion.

8. The method according to claim 1, wherein the adenoviral gene delivery vehicle is not replication-competent.

9. The method according to claim 1, wherein the nucleic acid payload lacks one or more functional adenoviral genes from the E1, E2, E3 or E4 regions.

10. The method according to claim 9, wherein the nucleic acid payload contains no functional adenoviral genes.

11. The method according to claim 1, wherein the nucleic acid payload comprises a heterologous gene encoding a cytokine, antibody, immunostimulatory factor, anti-angiogenic factor, angiogenic factor, anti-inflammatory protein, regulator of vascular remodelling, pro-apoptotic factor for vascular cells, or metalloprotease inhibitor.

12. The method according to claim 1, wherein the nucleic acid payload comprises a heterologous gene encoding a nucleic acid capable of hybridising to mRNA or DNA of a target gene or a nucleic acid capable of inhibiting expression of a target gene by co-suppression.

13. A method of gene delivery or gene transfer to a human smooth muscle cell (hSMC) comprising contacting the hSMC with an adenoviral gene delivery vehicle, wherein the adenoviral gene delivery vehicle comprises an Ad49 hexon protein, an Ad49 penton protein, an Ad49 fiber protein, and a nucleic acid payload comprising a heterologous gene, thereby providing a genetically modified hSMC.

14. The method according to claim 13, wherein the hSMC is obtained from a saphenous vein.

15. The method according to claim 13, further comprising introducing the genetically modified hSMC into a subject.

* * * * *

SEQUENCE LISTING

```
<160> NUMBER OF SEQ ID NOS: 3

<210> SEQ ID NO 1
<211> LENGTH: 953
<212> TYPE: PRT
<213> ORGANISM: Human adenovirus 49

<400> SEQUENCE: 1

Met Cys Leu Thr Ala Arg Glu Arg Ala Lys Met Ala Thr Pro Ser Met
1               5                   10                  15

Met Pro Gln Trp Ala Tyr Met His Ile Ala Gly Gln Asp Ala Ser Glu
            20                  25                  30

Tyr Leu Ser Pro Gly Leu Val Gln Phe Ala Arg Ala Thr Asp Thr Tyr
        35                  40                  45

Phe Ser Leu Gly Asn Lys Phe Arg Asn Pro Thr Val Ala Pro Thr His
    50                  55                  60

Asp Val Thr Thr Asp Arg Ser Gln Arg Leu Thr Leu Arg Phe Val Pro
65                  70                  75                  80

Val Asp Arg Glu Asp Thr Thr Tyr Ser Tyr Lys Ala Arg Phe Thr Leu
                85                  90                  95

Ala Val Gly Asp Asn Arg Val Leu Asp Met Ala Ser Thr Tyr Phe Asp
            100                 105                 110

Ile Arg Gly Val Leu Asp Arg Gly Pro Ser Phe Lys Pro Tyr Ser Gly
        115                 120                 125

Thr Ala Tyr Asn Ser Leu Ala Pro Lys Gly Ala Pro Asn Ser Ser Gln
    130                 135                 140

Trp Asp Ala Lys Glu Asn Asn Gly Gln Gly Glu Ala Lys Thr His Thr
145                 150                 155                 160

Tyr Gly Val Ala Ala Met Gly Gly Tyr Asn Ile Thr Lys Asp Gly Leu
                165                 170                 175

Gln Ile Gly Ile Asp Glu Asn Lys Glu Glu Asp Glu Glu Gly Arg Glu
            180                 185                 190

Ile Phe Ala Val Lys Ser Tyr Gln Pro Glu Pro Gln Val Gly Glu Glu
        195                 200                 205

Asn Trp Gln Asn Thr Glu Asn Phe Tyr Gly Arg Ala Leu Lys Lys
    210                 215                 220

Glu Thr Lys Met Lys Pro Cys Tyr Gly Ser Phe Ala Arg Pro Thr Asn
225                 230                 235                 240

Asp Lys Gly Gly Gln Ala Val Phe Lys Thr Gly Glu Asn Gly Lys Pro
                245                 250                 255

Thr Glu Glu Leu Asp Ile Asp Leu Ala Phe Phe Asp Leu Arg Gln Asn
            260                 265                 270

Asp Thr Gly Gly Asn Asn Asn Gln Pro Asp Met Ile Met Tyr Ala Glu
```

-continued

```
            275                 280                 285
Asn Val Asn Leu Glu Thr Pro Asp Thr His Val Val Tyr Lys Pro Gly
            290                 295                 300
Thr Ser Asp Asp Ser Ser Glu Ile Asn Leu Cys Gln Gln Ser Met Pro
305                 310                 315                 320
Asn Arg Pro Asn Tyr Ile Gly Phe Arg Asp Asn Phe Val Gly Leu Met
                    325                 330                 335
Tyr Tyr Asn Ser Thr Gly Asn Met Gly Val Leu Ala Gly Gln Ala Ser
                340                 345                 350
Gln Leu Asn Ala Val Val Asp Leu Gln Asp Arg Asn Thr Glu Leu Ser
                355                 360                 365
Tyr Gln Leu Leu Leu Asp Ser Leu Gly Asp Arg Thr Arg Tyr Phe Ser
            370                 375                 380
Met Trp Asn Ser Ala Val Asp Ser Tyr Asp Pro Asp Val Arg Ile Ile
385                 390                 395                 400
Glu Asn His Gly Val Glu Asp Glu Leu Pro Asn Tyr Cys Phe Pro Leu
                    405                 410                 415
Asp Gly Ser Gly Ser Ser Thr Ala Tyr Gln Gly Val Glu Pro Asp Thr
                420                 425                 430
Thr Val Ala Gly Thr Asn Asp Lys Trp Lys Val Asn Ala Lys Val Ala
            435                 440                 445
Gln His Asn Gln Ile Ala Lys Gly Asn Leu Phe Ala Met Glu Ile Asn
450                 455                 460
Leu Gln Ala Asn Leu Trp Lys Ser Phe Leu Tyr Ser Asn Val Ala Leu
465                 470                 475                 480
Tyr Leu Pro Asp Ser Tyr Lys Tyr Thr Pro Ala Asn Val Lys Leu Pro
                    485                 490                 495
Thr Asn Thr Asn Thr Tyr Asp Tyr Met Asn Gly Arg Val Val Ala Pro
                500                 505                 510
Ser Leu Val Asp Ala Tyr Ile Asn Ile Gly Ala Arg Trp Ser Leu Asp
            515                 520                 525
Pro Met Asp Asn Val Asn Pro Phe Asn His His Arg Asn Ala Gly Leu
            530                 535                 540
Arg Tyr Arg Ser Met Leu Leu Gly Asn Gly Arg Tyr Val Pro Phe His
545                 550                 555                 560
Ile Gln Val Pro Gln Lys Phe Phe Ala Ile Lys Asn Leu Leu Leu Leu
                    565                 570                 575
Pro Gly Ser Tyr Thr Tyr Glu Trp Asn Phe Arg Lys Asp Val Asn Met
                580                 585                 590
Ile Leu Gln Ser Ser Leu Gly Asn Asp Leu Arg Val Asp Gly Ala Ser
                595                 600                 605
Val Arg Phe Asp Ser Val Asn Leu Tyr Ala Thr Phe Phe Pro Met Ala
            610                 615                 620
His Asn Thr Ala Ser Thr Leu Glu Ala Met Leu Arg Asn Asp Thr Asn
625                 630                 635                 640
Asp Gln Ser Phe Asn Asp Tyr Leu Ser Ala Ala Asn Met Leu Tyr Pro
                    645                 650                 655
Ile Pro Ala Lys Ala Thr Asn Val Pro Ile Ser Ile Pro Ser Arg Asn
                660                 665                 670
Trp Ala Ala Phe Arg Gly Trp Ser Phe Thr Arg Leu Lys Thr Lys Glu
            675                 680                 685
Thr Pro Ser Leu Gly Ser Gly Phe Asp Pro Tyr Phe Val Tyr Ser Gly
            690                 695                 700
```

```
Ser Ile Pro Tyr Leu Asp Gly Thr Phe Tyr Leu Asn His Thr Phe Lys
705                 710                 715                 720

Lys Val Ser Ile Met Phe Asp Ser Ser Val Ser Trp Pro Gly Asn Asp
            725                 730                 735

Arg Leu Leu Thr Pro Asn Glu Phe Glu Ile Lys Arg Ser Val Asp Gly
        740                 745                 750

Glu Gly Tyr Asn Val Ala Gln Cys Asn Met Thr Lys Asp Trp Phe Leu
            755                 760                 765

Val Gln Met Leu Ser His Tyr Asn Ile Gly Tyr Gln Gly Phe His Val
770                 775                 780

Pro Glu Gly Tyr Lys Asp Arg Met Tyr Ser Phe Phe Arg Asn Phe Gln
785                 790                 795                 800

Pro Met Ser Arg Gln Val Val Asp Glu Ile Asn Tyr Lys Asp Tyr Lys
                805                 810                 815

Ala Val Thr Leu Pro Phe Gln His Asn Asn Ser Gly Phe Thr Gly Tyr
            820                 825                 830

Leu Ala Pro Thr Met Arg Gln Gly Gln Pro Tyr Pro Ala Asn Phe Pro
        835                 840                 845

Tyr Pro Leu Ile Gly Ser Thr Ala Val Pro Ser Val Thr Gln Lys Lys
850                 855                 860

Phe Leu Cys Asp Arg Val Met Trp Arg Ile Pro Phe Ser Ser Asn Phe
865                 870                 875                 880

Met Ser Met Gly Ala Leu Thr Asp Leu Gly Gln Asn Met Leu Tyr Ala
                885                 890                 895

Asn Ser Ala His Ala Leu Asp Met Thr Phe Glu Val Asp Pro Met Asp
            900                 905                 910

Glu Pro Thr Leu Leu Tyr Leu Leu Phe Glu Val Phe Asp Val Val Arg
        915                 920                 925

Val His Gln Pro His Arg Gly Val Ile Glu Ala Val Tyr Leu Arg Thr
930                 935                 940

Pro Phe Ser Ala Gly Asn Ala Thr Thr
945                 950

<210> SEQ ID NO 2
<211> LENGTH: 385
<212> TYPE: PRT
<213> ORGANISM: Human adenovirus 49

<400> SEQUENCE: 2

Met Ser Lys Arg Leu Arg Val Glu Asp Asp Phe Asn Pro Val Tyr Pro
1               5                   10                  15

Tyr Gly Tyr Ala Arg Asn Gln Asn Ile Pro Phe Leu Thr Pro Pro Phe
            20                  25                  30

Val Ser Ser Asp Gly Phe Gln Asn Phe Pro Pro Gly Val Leu Ser Leu
        35                  40                  45

Lys Leu Ala Asp Pro Ile Ala Ile Thr Asn Gly Asn Val Ser Leu Lys
    50                  55                  60

Val Gly Gly Gly Leu Thr Val Glu Gln Asp Ser Gly Asn Leu Lys Val
65                  70                  75                  80

Asn Pro Lys Ala Pro Leu Gln Val Ala Thr Asn Gln Leu Glu Ile
                85                  90                  95

Ser Leu Ala Asp Pro Phe Glu Val Lys Asn Lys Lys Leu Ser Leu Lys
            100                 105                 110

Val Gly His Gly Leu Lys Val Ile Asp Glu Asn Ile Ser Thr Leu Gln
```

```
            115                 120                 125
Gly Leu Leu Gly Asn Leu Val Leu Thr Gly Met Gly Ile Gly Thr
    130                 135                 140
Glu Glu Leu Lys Lys Asp Asp Lys Ile Val Gly Ser Ala Val Asn Val
145                 150                 155                 160
Arg Leu Gly Gln Asp Gly Gly Leu Thr Phe Asp Lys Lys Gly Asp Leu
                165                 170                 175
Val Ala Trp Asn Lys Glu Asn Asp Arg Arg Thr Leu Trp Thr Thr Pro
            180                 185                 190
Asp Pro Ser Pro Asn Cys Lys Val Ser Glu Glu Lys Asp Ser Lys Leu
        195                 200                 205
Thr Leu Val Leu Thr Lys Cys Gly Ser Gln Ile Leu Ala Ser Val Ser
    210                 215                 220
Leu Leu Val Val Lys Gly Lys Phe Ala Asn Ile Asn Asn Lys Thr Asn
225                 230                 235                 240
Pro Gly Glu Asp Tyr Lys Lys Phe Ser Val Lys Leu Leu Phe Asp Ala
                245                 250                 255
Asn Gly Lys Leu Leu Thr Gly Ser Ser Leu Asp Gly Asn Tyr Trp Asn
            260                 265                 270
Tyr Lys Asn Lys Asp Ser Val Ile Gly Ser Pro Tyr Glu Asn Ala Val
        275                 280                 285
Pro Phe Met Pro Asn Ser Thr Ala Tyr Pro Lys Ile Ile Asn Asn Gly
    290                 295                 300
Thr Ala Asn Pro Glu Asp Lys Lys Ser Ala Lys Lys Thr Ile Val
305                 310                 315                 320
Thr Asn Val Tyr Leu Gly Gly Asp Ala Ala Lys Pro Val Ala Thr Thr
                325                 330                 335
Ile Ser Phe Asn Lys Glu Thr Glu Ser Asn Cys Val Tyr Ser Ile Thr
            340                 345                 350
Phe Asp Phe Ala Trp Asn Lys Thr Tyr Lys Asn Val Pro Phe Asp Ser
        355                 360                 365
Ser Ser Leu Thr Phe Ser Tyr Ile Ala Gln Asp Ala Glu Asp Lys Asn
    370                 375                 380
Glu
385

<210> SEQ ID NO 3
<211> LENGTH: 519
<212> TYPE: PRT
<213> ORGANISM: Human adenovirus 49

<400> SEQUENCE: 3

Met Arg Arg Ala Val Val Ser Ser Ser Pro Pro Ser Tyr Glu Ser
1               5                   10                  15
Val Met Ala Gln Ala Thr Leu Glu Val Pro Phe Val Pro Arg Tyr
                20                  25                  30
Met Ala Pro Thr Glu Gly Arg Asn Ser Ile Arg Tyr Ser Glu Leu Ala
            35                  40                  45
Pro Gln Tyr Asp Thr Thr Arg Val Tyr Leu Val Asp Asn Lys Ser Ala
        50                  55                  60
Asp Ile Ala Ser Leu Asn Tyr Gln Asn Asp His Ser Asn Phe Leu Thr
65                  70                  75                  80
```

```
Thr Val Val Gln Asn Asn Asp Phe Thr Pro Ala Glu Ala Ser Thr Gln
                85                  90                  95

Thr Ile Asn Phe Asp Glu Arg Ser Arg Trp Gly Gly Asp Leu Lys Thr
            100                 105                 110

Ile Leu His Thr Asn Met Pro Asn Val Asn Glu Tyr Met Phe Thr Ser
            115                 120                 125

Lys Phe Lys Ala Arg Val Met Val Ser Arg Lys Arg Pro Glu Gly Ala
        130                 135                 140

Thr Asp Ala Ser Gln Asp Ile Leu Lys Tyr Glu Trp Phe Glu Phe Thr
145                 150                 155                 160

Leu Pro Glu Gly Asn Phe Ser Glu Thr Met Thr Ile Asp Leu Met Asn
                165                 170                 175

Asn Ala Ile Leu Glu Asn Tyr Leu Gln Val Gly Arg Gln Asn Gly Val
            180                 185                 190

Leu Glu Ser Asp Ile Gly Val Lys Phe Asp Ser Arg Asn Phe Arg Leu
        195                 200                 205

Gly Trp Asp Pro Glu Thr Lys Leu Val Met Pro Gly Val Tyr Thr Tyr
    210                 215                 220

Glu Ala Phe His Pro Asp Val Val Leu Leu Pro Gly Cys Gly Val Asp
225                 230                 235                 240

Phe Thr Glu Ser Arg Leu Ser Asn Leu Leu Gly Ile Arg Lys Lys Gln
                245                 250                 255

Pro Phe Gln Glu Gly Phe Arg Ile Met Tyr Glu Asp Leu Glu Gly Gly
            260                 265                 270

Asn Ile Pro Ala Leu Leu Asp Val Glu Ala Tyr Leu Lys Ser Lys Asn
        275                 280                 285

Asp Leu Glu Glu Ala Thr Lys Asn Ala Asn Arg Ala Ala Ala Asn Gly
    290                 295                 300

Gly Gly Glu Thr Arg Gly Asp Thr Phe Leu Thr Thr Glu Gln Leu Arg
305                 310                 315                 320

Ala Ala Gly Lys Glu Leu Val Ile Lys Pro Ile Lys Glu Asp Ala Ser
                325                 330                 335

Lys Arg Ser Tyr Asn Val Ile Gly Asp Thr His Asp Thr Leu Tyr Arg
            340                 345                 350

Ser Trp Tyr Leu Ser Tyr Thr Tyr Gly Asp Pro Glu Lys Gly Val Gln
        355                 360                 365

Ser Trp Thr Leu Leu Thr Thr Pro Asp Val Thr Cys Gly Ala Glu Gln
    370                 375                 380

Val Tyr Trp Ser Leu Pro Asp Leu Met Gln Asp Pro Val Thr Phe Arg
385                 390                 395                 400

Ser Thr Gln Gln Val Ser Asn Tyr Pro Val Val Gly Ala Glu Leu Met
                405                 410                 415

Pro Phe Arg Ala Lys Ser Phe Tyr Asn Asp Leu Ala Val Tyr Ser Gln
            420                 425                 430

Leu Ile Arg Ser Tyr Thr Ser Leu Thr His Val Phe Asn Arg Phe Pro
        435                 440                 445

Asp Asn Gln Ile Leu Cys Arg Pro Pro Ala Pro Thr Ile Thr Thr Val
    450                 455                 460

Ser Glu Asn Val Pro Ala Leu Thr Asp His Gly Thr Leu Pro Leu Arg
465                 470                 475                 480
```

```
Ser Ser Ile Arg Gly Val Gln Arg Val Thr Val Thr Asp Ala Arg Arg
            485                 490                 495

Arg Thr Cys Pro Tyr Val Tyr Lys Ala Leu Gly Ile Val Ala Pro Arg
            500                 505                 510

Val Leu Ser Ser Arg Thr Phe
        515
```